United States Patent [19]
Mueller et al.

[11] Patent Number: 5,654,453
[45] Date of Patent: Aug. 5, 1997

[54] PROCESS FOR THE PRODUCTION OF α-BRANCHED ALIPHATIC MONOCARBOXYLIC ACIDS

[75] Inventors: Gerhard Mueller, Duesseldorf; Bernhard Gutsche, Hilden; Karl-Heinz Schmid, Mettmann; Frank Bongardt, Duesseldorf; Lutz Jeromin; Eberhard Peukert, both of Hilden; Hermann Frankenbach, Heideck, all of Germany

[73] Assignee: Henkel Kommanditgesellschaft auf Aktien, Duesseldorf, Germany

[21] Appl. No.: 500,905

[22] PCT Filed: Jan. 21, 1994

[86] PCT No.: PCT/EP94/00155

§ 371 Date: Aug. 29, 1995

§ 102(e) Date: Aug. 29, 1995

[87] PCT Pub. No.: WO94/17026

PCT Pub. Date: Aug. 4, 1994

[30] Foreign Application Priority Data

Jan. 29, 1993 [DE] Germany .................. 43 02 463.7

[51] Int. Cl.$^6$ .................................................. C07C 51/16
[52] U.S. Cl. .................................................. 554/132
[58] Field of Search .................................................. 554/132

[56] References Cited

U.S. PATENT DOCUMENTS 2,293,649  8/1942  Howk et al. .................... 260/413

FOREIGN PATENT DOCUMENTS

| 031694 | 3/1981 | European Pat. Off. . |
| 0031694 | 7/1981 | European Pat. Off. . |
| 2357865 | 5/1974 | Germany . |
| 2320461 | 11/1974 | Germany . |
| 1174975 | 12/1969 | United Kingdom . |

*Primary Examiner*—Deborah D. Carr
*Attorney, Agent, or Firm*—Wayne C. Jaeschke; John E. Drach; Henry E. Millson, Jr.

[57] ABSTRACT

A process is disclosed for preparing α-branched aliphatic monocarboxylic acids with 12 to 48 carbon atoms. In a first step of the process (a), α-branched aliphatic monohydric alcohols (Guerbet alcohols) are converted in the presence of caustic alkali into the alkali salts of the corresponding α-branched aliphatic monocarboxylic acids. In a second step of the process (b), the α-branched aliphatic monocarboxylic acids are released from the alkali salts by soap splitting in the presence of an inert diluting agent.

10 Claims, No Drawings

PROCESS FOR THE PRODUCTION OF α-BRANCHED ALIPHATIC MONOCARBOXYLIC ACIDS

BACKGROUND OF THE INVENTION

1. Field of the Invention

This application is a 371 of PCT/EP94/00155 filed Jan. 21, 1994.

This invention relates to a process for the production of α-branched aliphatic monocarboxylic acids containing 12 to 48 carbon atoms. In a first stage of the process (stage a), α-branched aliphatic monohydric alcohols (Guerbet alcohols) are converted into the alkali metal salts of the corresponding α-branched aliphatic monocarboxylic acids in the presence of alkali metal hydroxide and, in a second stage of the process (stage b), the α-branched aliphatic monocarboxylic acids are released from the alkali metal salts by soap decomposition.

2. Statement of Related Art

In the oleochemical industry, α-branched alcohols corresponding to the formula:

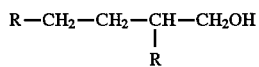

in which R is a $C_{4-20}$ hydrocarbon radical, are prepared from unbranched, saturated primary alcohols $R-CH_2-CH_2OH$ by the Guerbet reaction.

These alcohols and their derivatives are used in a number of formulations in the lubricant industry, in cosmetics and in textile care.

In the case of the fatty acids, it has not hitherto been possible to produce similarly branched products on an industrial scale although there are corresponding potential applications for these fatty acids and their derivatives. The esters with polyhydric alcohols, such as pentaerythritol or trimethylol propane, are distinguished with particular advantage by low vapor pressures and low pour points.

Accordingly, there has been no shortage of attempts to find production processes for the branched fatty acids.

In a process of the type mentioned at the beginning which is described in DE-A-2 320 461, Guerbet alcohols are first reacted with alkali to form the carboxylic acid salts. The corresponding monocarboxylic acid is then prepared by soap decomposition with mineral acids. The first stage of this process is carried out in an oxidative alkali melt at correspondingly high temperatures. In view of the melting points of NaOH and KOH, which are used for economic reasons, operating temperatures of more than 370° C. have to be applied.

The pour points of the soaps, which have to be present in liquid form according to this prior art so that thay may be separated from the reaction mixture, are also above 340° C. The hydrogen formed during the reaction leads to safety problems in view of the elevated temperature. Besides blockages of pipelines, the highly corrosive effect of the alkali melt on virtually all known materials is a major obstacle to the operation of this process on an industrial scale.

In a process for the production of salts of carboxylic acids from the corresponding alcohols and a base, which is known from EP 31 694 B1, the formation of solid reaction products and the foaming of the reaction mixture during the alkaline oxidation of the alcohols are prevented by the use of inert viscosity reducers. A mixture of the base and a catalyst in an inert diluting liquid is introduced before the beginning of the reaction. The alcohol to be reacted is only added to this mixture thereafter under the reaction conditions. However, addition of the diluent before the reaction leads to a reduction in the volume/time yield to values of 20 to 80%.

The sole object of adding water, as mentioned in the Comparison Examples of EP 31 694 B1, is to decelerate the saponification reaction and hence the formation of hydrogen and thus to prevent foaming. The criterion mentioned in EP 31 694 B1 with regard to the choice of the diluent is the low volatility under the reaction conditions so that the diluent remains in the liquid phase.

DESCRIPTION OF THE INVENTION

The problem addressed by the present invention was to provide an industrially workable process in which the above-mentioned problem of foaming would be solved without having to accept the disadvantage of a reduction in the volume/time yield. Accordingly, the process according to the invention is characterized in that stage a of the process, i.e. conversion of the Guerbet alcohols into the alkali metal salts of the corresponding monocarboxylic acids, is carried out as a reaction between solid alkali metal hydroxide and liquid alcohol and an inert diluent is added to the reaction mixture on completion of this reaction in order to reduce the viscosity. In a particularly preferred embodiment, the process is carried out continuously.

The choice of the viscosity reducer and diluent is preferably determined by the derivatization carried out after the preparation of the salts of the branched monocarboxylic acids.

In the process according to the invention, the starting materials are introduced into the reactor together and completely in the cold state. The alkali, preferably NaOH in solid form, can be accurately dosed without difficulty in contrast to the melt process mentioned above.

The reaction between liquid alcohol and the solid alkali metal hydroxide begins during heating at a reactor temperature of only 200° to 250° C. Hydrogen is released during the reaction, leaving the reactor in gaseous form. The temperatures towards the end of the reaction also are below the temperatures for an alkali melt in order to avoid the known corrosive effect. The reactors can thus be made of inexpensive materials. The temperatures on completion of the reaction phase are between 250° and 350° C. The pour points of the pure soaps are thus not exceeded in some cases. Solidification of the soap before the end of the reaction is avoided by the alcohol still present. Finally, when the yield reaches 98% or more, based on the alcohol used, there is a pronounced increase in viscosity. Only then is an inert diluent added to the reaction mixture to keep it manageable and to reduce the pour point of the reaction products. Small dissolved quantities of water of around 1 to 5% by weight are sufficient at temperatures above 200° C.

Most of the steam introduced on completion of the reaction at 250° to 350° C. to reduce the viscosity leaves the reaction zone in vapor form and only leads to cooling and an increase in water solubility after condensation and re-evaporation.

In contrast to the prior art, therefore, the process according to the invention is based on a solid/liquid reaction in which the temperatures are below the temperatures for an alkali melt. In one particular embodiment, the alkali metal hydroxide is suspended in the liquid alcohol in stage a of the process, i.e. conversion of the Guerbet alcohols into the alkali metal salts of the corresponding monocarboxylic acids.

Where the solid/liquid reaction is carried out in accordance with the invention in the presence of an inert diluent to reduce the viscosity, alkali metal hydroxide and Guerbet alcohol are preferably introduced cold into the reactor, the reaction mixture is gradually heated from around room temperature to the reaction temperature and, on completion of the reaction, the reaction mixture is cooled by addition of the diluent. The reaction is preferably carried out at temperatures of at most 350° C. The temperatures may be between 250° and 350° C.

In one embodiment of the invention, a substance evaporating at the reaction temperature, more particularly water, is used as the coolant and diluent. Not only is water very suitable for keeping the reaction mixture liquid, it also enables the reaction mixture to be cooled very quickly to temperatures below 200° C. In another embodiment of the invention, therefore, the reaction mixture is cooled to temperatures below 200° C. The water may be added in various ways. It has proved to be of particular advantage to inject steam into the reaction zone and to spray in liquid water.

The addition of 5 to 30% by weight of water to the reaction mixture is sufficient to keep the soaps formed liquid, even at room temperature. After decomposition of the soaps, the water introduced may be completely removed by simple phase separation.

During cooling of the reaction mixture by addition of water, the greater part of the water evaporates in accordance with the phase equilibrium between soap and water. In another advantageous embodiment, the water evaporated is condensed and returned to the reaction mixture.

In another embodiment of the process according to the invention, the reaction is carried out under excess pressure, more particularly under a pressure of up to 10 bar, to reduce the gas velocity of the hydrogen formed and hence foaming. The reaction is preferably carried out in an inert gas atmosphere, for example of nitrogen.

In addition, the economy of the process is increased if the hydrogen of reaction formed in the first stage, i.e. conversion of the Guerbet alcohols into the corresponding monocarboxylic acids, is collected and used. More particularly, it may be used as a combustible gas.

After the reaction of the reaction mixture to form the salts of the branched monocarboxylic acids, the soaps formed are decomposed. Since only stoichiometric quantities of alkali are used in the process according to the invention, the soap does not have to be separated from the alkali in the reactor, instead it may remain in the reactor for decomposition.

Decomposition of the soaps may be carried out as described in the literature. To this end, sulfuric acid or hydrochloric acid, for example, may be used under normal pressure. However, the soaps may also be decomposed under pressure in the process according to the present invention.

EXAMPLES

The following Examples are intended to illustrate the invention without limiting it in any way.

Example 1: Preparation of Isopalmitic Acid

A stirred reactor was used. The periphery consists of a dephlegmator, a condenser and a phase separator.

8,000 kg of 2-hexyl decanol and 1,280 kg of NaOH were introduced cold into the reactor and heated under normal pressure. The reaction began with evolution of hydrogen at a reactor temperature of 230° C. On reaching a temperature of 310° C., the evolution of hydrogen abated and the viscosity underwent a drastic increase. The cooling phase was then started by the injection of steam at 140° C. through a submerged pipe. Part of the steam remained in reactor to reduce the viscosity. In accordance with the soap/water phase equilibrium, the greater part of the water left the reactor in vapor form and was condensed in dephlegmator. The condensate ran back into the reactor and removed heat from the reactor through evaporation. The soap solution formed was then decomposed with 1,500 kg of $H_2SO_4$ at 80° C. to form the isopalmitic acid.

Approximately 7,800 kg of reaction product with an acid value of 200 and a hydroxyl value of <3 were obtained. During the reaction phase, around 400 kg of distillate were collected and reused as starting material in further tests.

Example 2: Production of Isopalmitic Acid Under Elevated Pressure

The starting materials were initially introduced as described in Example 1. However, a nitrogen pressure of 4 bar was established in the reactor before heating. The further process was carried out as in Example 1 and 8,150 kg of product (acid value 201, OH value <3) and around 50 kg of distillate were obtained.

Example 3: Production of Isopalmitic Acid Preceded by Guerbetization 180 kg of octanol, 4.5 kg of KOH and 80 g of ZnO were introduced into a 350 liter reactor. The reactor was heated to 200° C. After the beginning of the reaction, an octanol/water mixture was removed after the condenser and the alcohol phase was returned to the reactor. During the reaction, the reactor temperature rose to 250° C. After the removal of water, the reaction mixture was found by GC analysis to contain about 8% of octanol, 78% of 2-hexyl decanol and about 8% of 2,4-dihexyl dodecanol. The octanol content was reduced to below 1% by distillation at 240° C./100 mbar. After venting to normal pressure, 24 kg of NaOH were introduced into the reactor and the reaction was continued as in Example 1.

135 kg of a product with an acid value of 205 and an OH value of <3 were obtained in this test. 25.2 kg consisting of equal parts of octanol and Guerbet alcohol were removed during the distillation. The distillate may be used as starting material for further reactions.

Example 4: Production of Isotridecanoic Acid 180 kg of isotridecyl alcohol and 33.6 kg of NaOH were introduced into the 350 liter reactor and heated to 340° C. under a nitrogen pressure of 6 bar. The process was otherwise carried out as described in Example 1. The product obtained had an acid value of 240 and an OH value of 6.3.

Example 5: Production of Isocerotic Acid 180 kg of lauryl and myristyl alcohol in equal parts were introduced into the reactor together with 1.34 kg of KOH and 80 g of ZnO. In the same process as in Example 3, distillation produced about 25 kg of mixed alcohol consisting of equal parts of monomers and dimers. The product obtained after decomposition (145 kg) had an acid value of 148 and an OH value of <2. According to GC analysis, 19% of this mixture consisted of isotetracosanoic acid, 51% of isohexacosanoic acid (isocerotic acid) and 25% of isooctacosanoic acid.

Example 6: Production of Isopalmitic Acid (Soap Decomposition with Carbon Dioxide)

The process was carried out as described in Example 1 as far as the soap solution. The product was then diluted in a ratio of 2 parts of water to 1 part of soap and introduced into an autoclave. The mixture was stirred for 2 hours at 30° C. under a $CO_2$ pressure of 60 bar. After phase separation, an acid value of 189.2 was measured in the fatty phase.

What is claimed is:

1. A process for the production of α-branched aliphatic monocarboxylic acids having 12 to 48 carbon atoms comprising the steps of: (a) reacting a liquid α-branched aliphatic monohydric alcohol and an alkali metal hydroxide in the absence of an inert diluent to produce a reaction mixture comprising an alkali metal salt of the corresponding α-branched aliphatic monocarboxylic acid; (b) adding an inert diluent to said reaction mixture after completion of the reaction to reduce the viscosity thereof; (c) releasing the α-branched aliphatic monocarboxylic acid from the reaction mixture of step (b) by salt decomposition.

2. The process of claim 1 wherein said alkali metal hydroxide is a solid.

3. The process of claim 1 wherein said alkali metal hydroxide is suspended in said liquid alcohol.

4. The process of claim 1 wherein step (a) is carried out at a temperature of up to about 350° C.

5. The process of claim 1 wherein said diluent is water.

6. The process of claim 1 wherein the addition of said diluent cools said reaction mixture to a temperature of less than about 200° C.

7. The process of claim 1 wherein said diluent is steam.

8. The process of claim 1 wherein from about 5 to about 30% by weight of water is added to the reaction mixture in step (b).

9. The process of claim 1 further comprising the step of condensing and recycling any evaporated diluent formed in the step (b).

10. The process of claim 1 wherein step (a) is carried out under a pressure of up to about 10 bar.

* * * * *